United States Patent
Bhetariya et al.

(10) Patent No.: US 9,290,817 B2
(45) Date of Patent: Mar. 22, 2016

(54) DIAGNOSTIC ASSAYS FOR THE DETECTION AND IDENTIFICATION OF ASPERGILLI

(75) Inventors: Preetida Jagdish Bhetariya, New Delhi (IN); Taruna Madan Gupta, Mumbai (IN); Yogendra Singh, New Delhi (IN); Anupam Varma, New Delhi (IN); Puranam Usha Sarma, New Delhi (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 182 days.

(21) Appl. No.: 13/817,692

(22) PCT Filed: Aug. 12, 2011

(86) PCT No.: PCT/IB2011/001854
§ 371 (c)(1),
(2), (4) Date: Jun. 19, 2013

(87) PCT Pub. No.: WO2012/023020
PCT Pub. Date: Feb. 23, 2012

(65) Prior Publication Data
US 2013/0266941 A1 Oct. 10, 2013

(30) Foreign Application Priority Data
Aug. 19, 2010 (IN) .......................... 0375/DEL/2010

(51) Int. Cl.
*C07H 21/04* (2006.01)
*C12Q 1/68* (2006.01)
*C12P 19/34* (2006.01)
*C07K 14/38* (2006.01)

(52) U.S. Cl.
CPC .............. *C12Q 1/6895* (2013.01); *C07K 14/38* (2013.01); *C07H 21/04* (2013.01)

(58) Field of Classification Search
None
See application file for complete search history.

(56) References Cited

U.S. PATENT DOCUMENTS 7,504,490 B1   3/2009  Weinstock et al. .......... 536/23.1

OTHER PUBLICATIONS

Ehrlich et al. Aspergillus flavus isolate 91077d polyketide synthase (pksA) gene, partial cds. GenBank Accession No. AY501892, 1000 bp (2004), pp. 1-2.*
Lowe et al. A computed program for selection of oligonucleotide primers for polymerase chain reactions. Nucleic Acids Res. (1990) vol. 18, No. 7, pp. 1757-1761.*
"Aspergillus fumigatus Af293 conserved hypothetical protein, partial mRNA", XP-002664849, retrieved from Geneseq Database accession No. XM_745383: Feb. 27, 2008.
"Aspergillus flavus NRRL3357 polyketide synthase PksP, mRNA", XP-002664850, retrieved from Geneseq Database accession No. XM_002382776: Jan. 19, 2010.
"Aspergillus niger CBS 513.88 hypothetical protein (An18g00520) partial mRNA", XP-002664851, Database accession No. XM_001398484: Feb. 28, 2008.
"Aspergillus fumigatus Af293 conidial pigment polyketide synthase PksP/Alb1 (AFUA_2G17600), partial mRNA", XP-002664852, retrieved from Geneseq Database accession No. XM_751002: Feb. 27, 2008.
Bhetariya, P. J. et al: "Multiplex PCR for Detection of Aspergillus fumigatus, Aspergillus flavus and Aspergillus niger", *Journal of Allergy and Clinical Immunology*, 123: 2, p. S160, (Feb. 2009).
"Sequence 10515 from U.S. Pat. No. 7504490", XP-002664853, retrieved from EBI accession No. EMBL:GP256179: Apr. 30, 2009.
"Aspergillus flavus NRRL3357 aflC / pksA / pksL1 / polyketide synthase, mRNA", XP-002664854, Database accession No. XM_002379910: Jan. 19, 2010.
Logotheti, M. et al: "Multiplex PCR for the discrimination of A. fumigatus, A. flavus, A. niger and A. terreus", *Journal of Microbiological Methods*, 76:2, pp. 209-211, (Feb. 2009).

* cited by examiner

*Primary Examiner* — Kenneth R. Horlick
*Assistant Examiner* — David Thomas
(74) *Attorney, Agent, or Firm* — Drinker Biddle & Reath LLP

(57) ABSTRACT

Three important species of *Aspergillus*, *A. fumigatus*, *A. flavus* and *A. niger* are known to contribute to the pathogenicity of allergic and invasive diseases in humans. They are also known to be plant pathogens. Several important ESTs/genes of *Aspergilli* species are now identified and characterized. Efforts are still needed to explore 30% genes of *Aspergillus* species for their valuable products which need to be explored. Polyketide biosynthetic pathway in *Aspergillus* species produce important secondary metabolites like polyketide toxins such as Aflatoxins, drugs such as Lovastatins and several other important pharmaceutically important polyketide compounds etc. With the availability of *Aspergillus* genome sequences it is possible today to characterize the structure and function of important genes of *Aspergillus* species. Based on the gene sequence information on PKS enzymes in medically and agriculturally important *Aspergillus* species such as *A. fumigatus*, *A. flavus* and *A. niger* sequences of diagnostic use are identified and a multiplex PCR assay is developed using clinical and agricultural samples.

4 Claims, 12 Drawing Sheets

Fig 1 (a): KS F-R primers gradient PCR with A. *fumigatus*
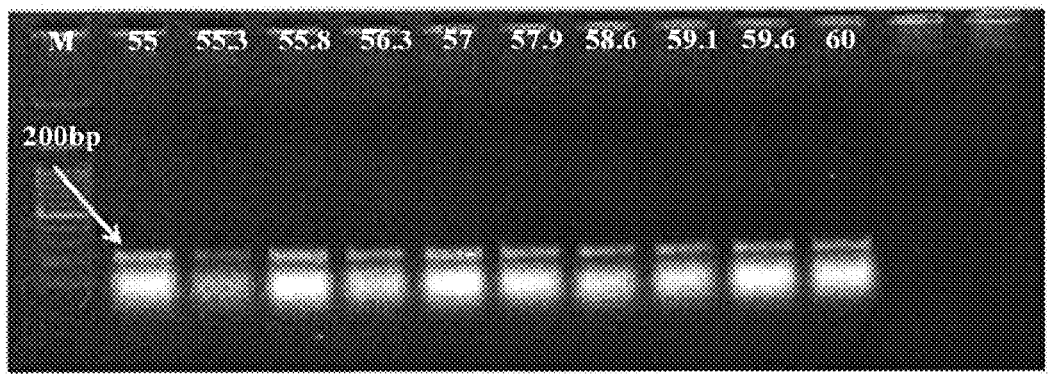
Fig 1 (b): KS F-R primers gradient PCR with A. *flavus*
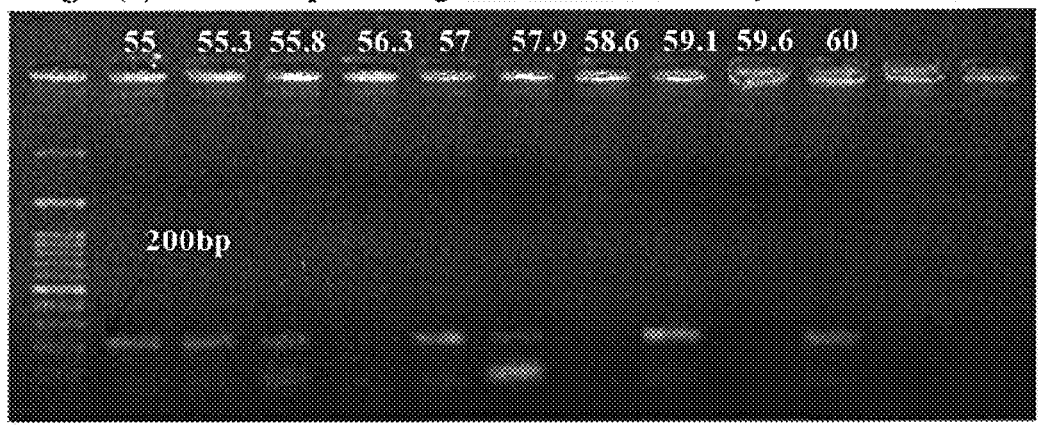
Fig 1 (c): KS F-R primers gradient PCR with A. *niger*
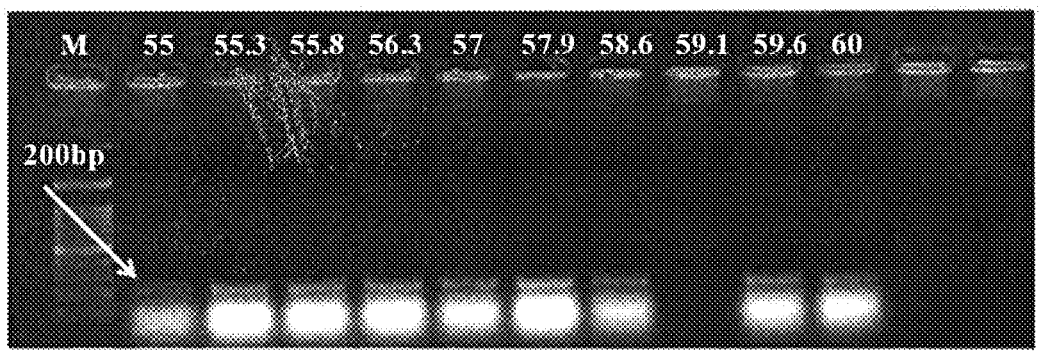

Fig 2 (a): Specific amplification of
*A. fumigatus*, *A. flavus* and *A. niger* using specific primers
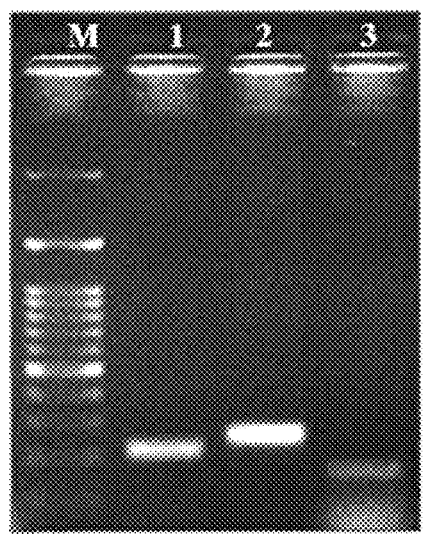
M: 100 bp ladder
Lane 1: *A. fumigatus*
Lane 2: *A. flavus*
Lane 3: *A. niger*

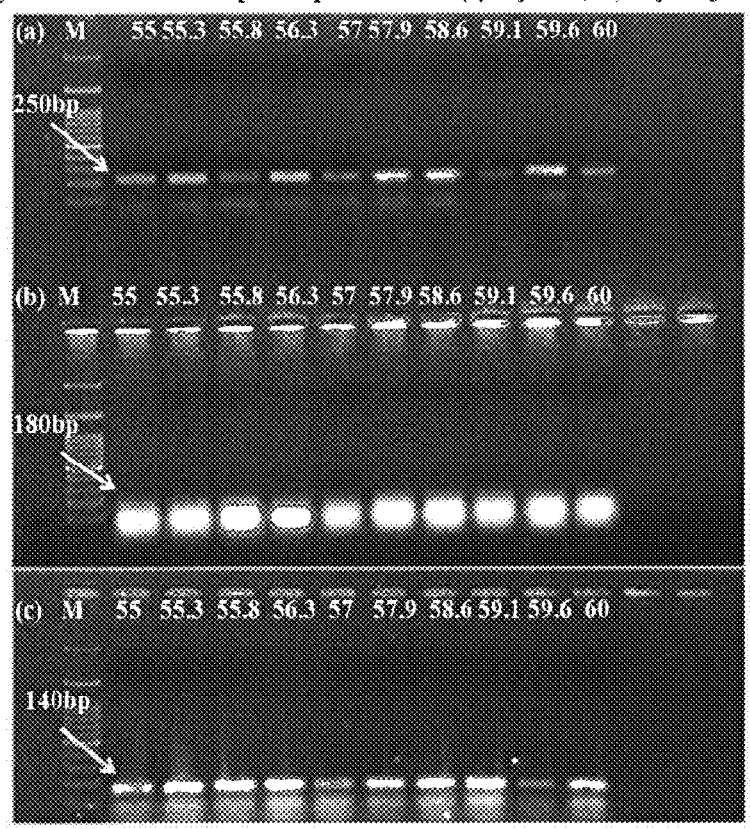
Fig 2 (b) : Gradient PCR for specific primers with (a) *A. flavus*, (b) *A. fumigatus* and (c) *A. niger*

Fig 3: Multiplex PCR for *A. fumigatus*, *A. flavus* and *A. niger*
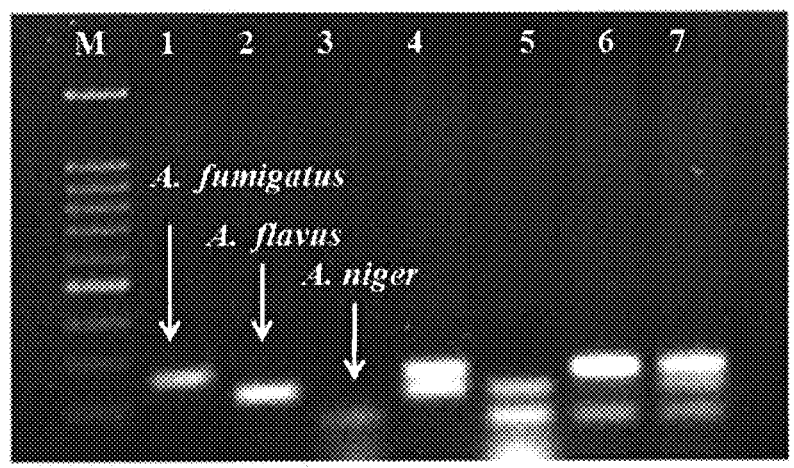
M: 100 bp marker
1: *A. fumigatus*
2: *A. flavus*
3: *A. niger*
4: *A. fumigatus* + *A. flavus*
5: *A. flavus* + *A. niger*
6: *A. niger* + *A. fumigatus*
7: *A. fumigatus* + *A. flavus* + *A. niger*

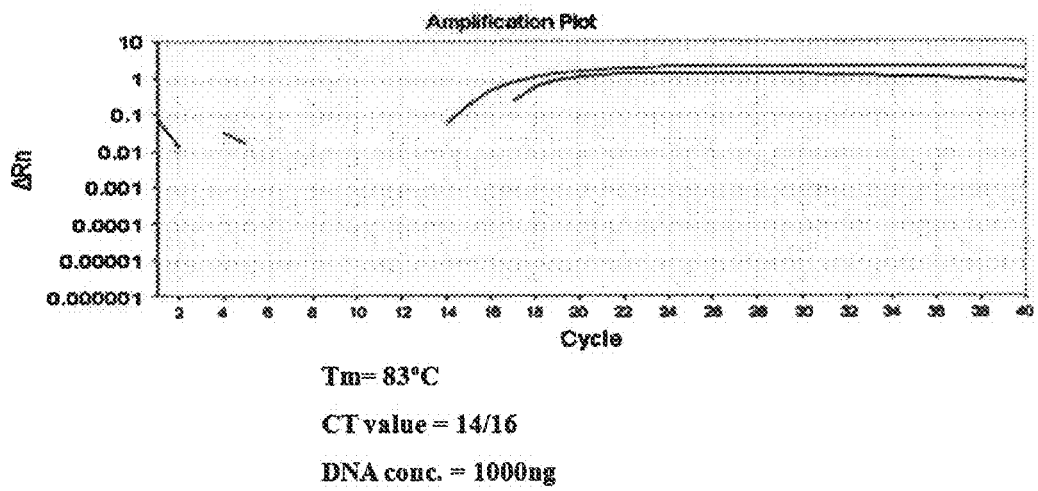
Fig 4 (a) : *Aspergillus fumigatus* specific SYBR green Real time PCR
Tm = 83°C
CT value = 14/16
DNA conc. = 1000ng
Fig 4 (b) : Melting curve of *Aspergillus fumigatus* specific SYBR green Real time PCR
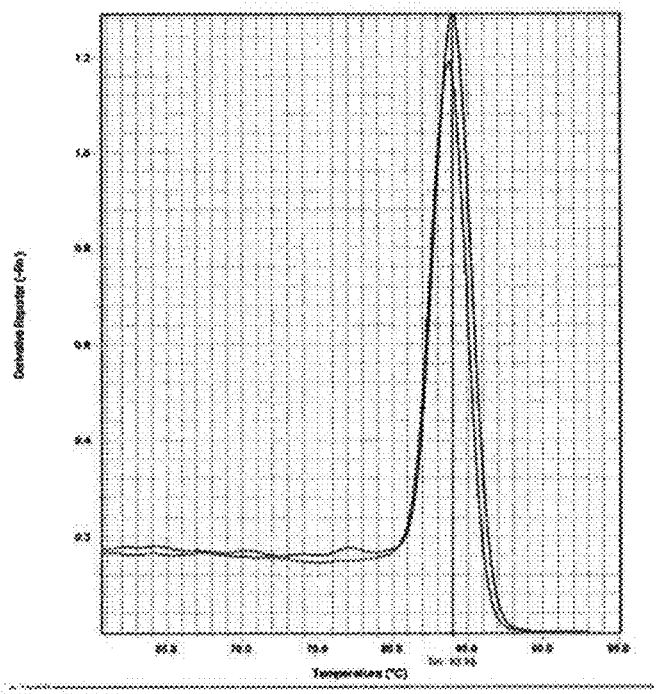

Fig 4 (c): *Aspergillus fumigatus* specific (probe Afu 5' 6-FAM & 3' BHQ) Absolute amplification curve
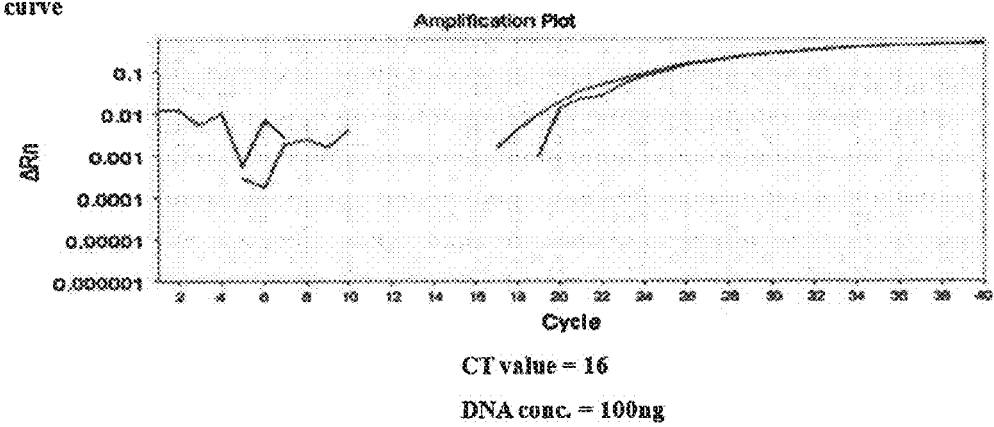
CT value = 16
DNA conc. = 100ng Fig 5 (a): *Aspergillus flavus* specific SYBR green real time PCR
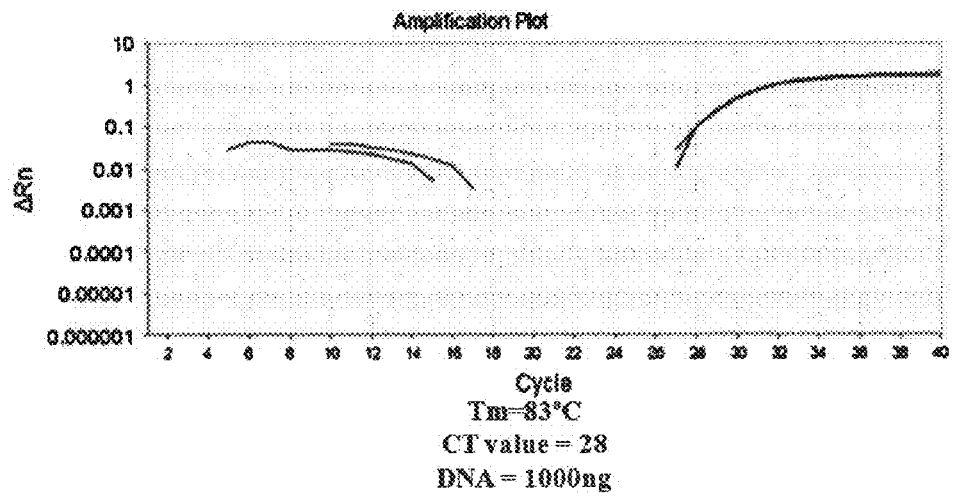
Tm=83°C
CT value = 28
DNA = 1000ng
Fig 5 (b): Melting curve of *Aspergillus flavus* specific SYBR green real time PCR
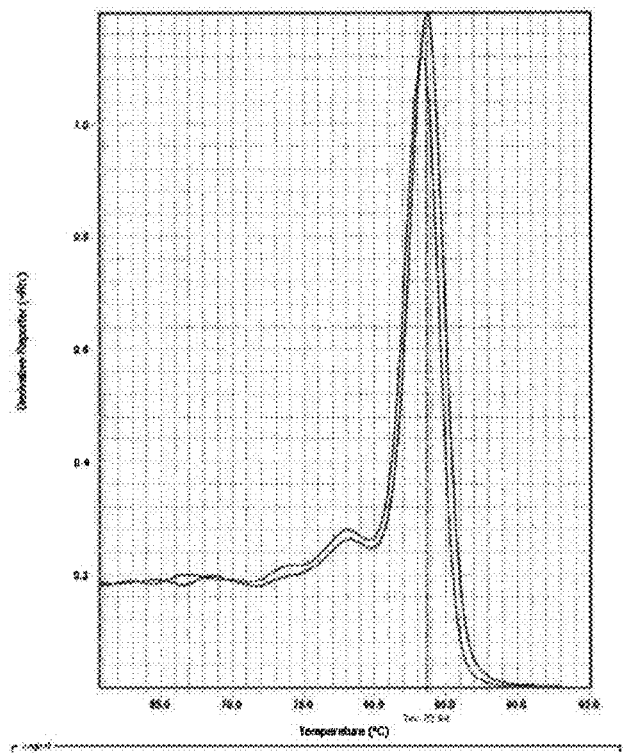

Fig 5 (c): *Aspergillus flavus* specific (probe Afl 5' HEX and 3'BHQ) Absolute amplification curve
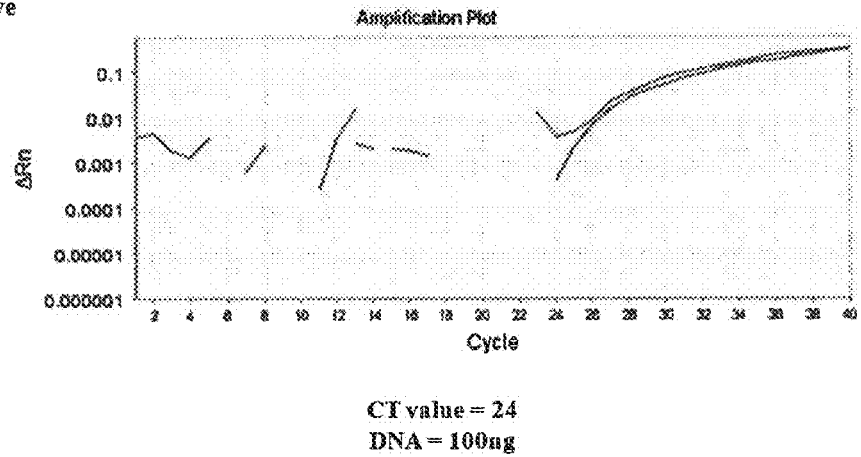
CT value = 24
DNA = 100ng Fig 6(a): *Aspergillus niger* specific SYBR green Real time PCR
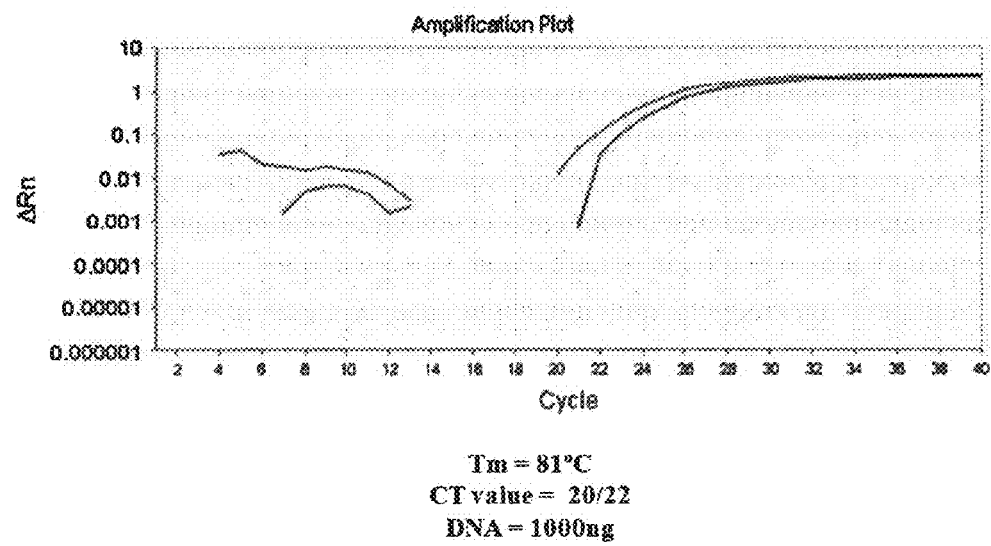
Tm = 81°C
CT value = 20/22
DNA = 1000ng
Fig 6 (b): Melting curve of *Aspergillus niger* specific SYBR green Real time PCR
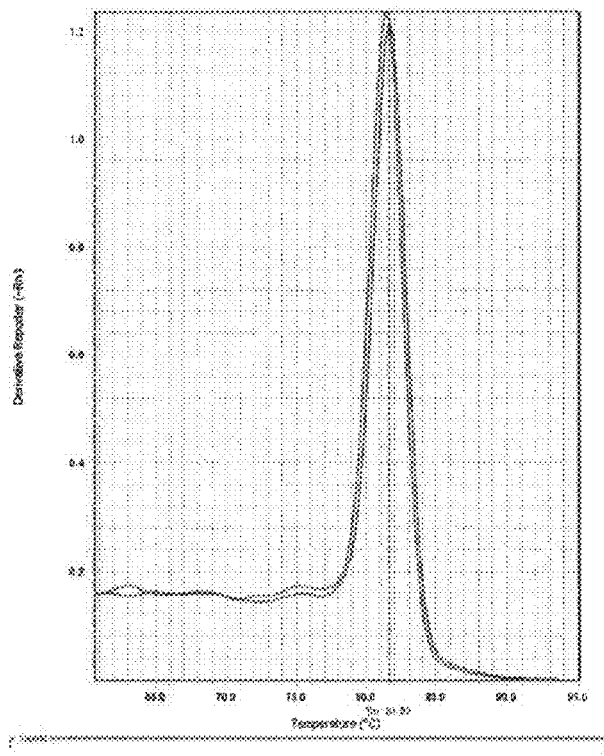

Fig 6 (c): *Aspergillus niger* specific (probe 5' Ani TET and 3' BHQ) Absolute amplification curve
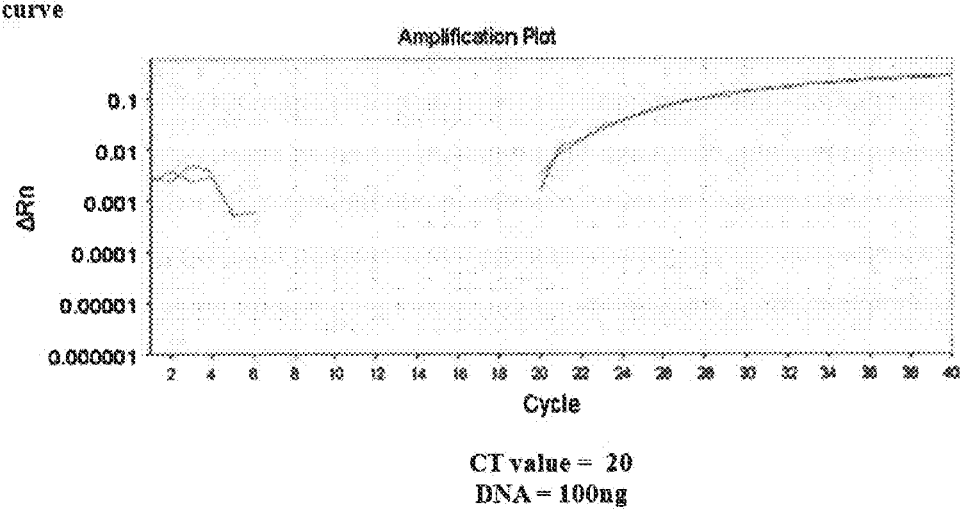
CT value = 20
DNA = 100ng Fig 7 (a): Aspergillus genus specific SYBR green Real time PCR
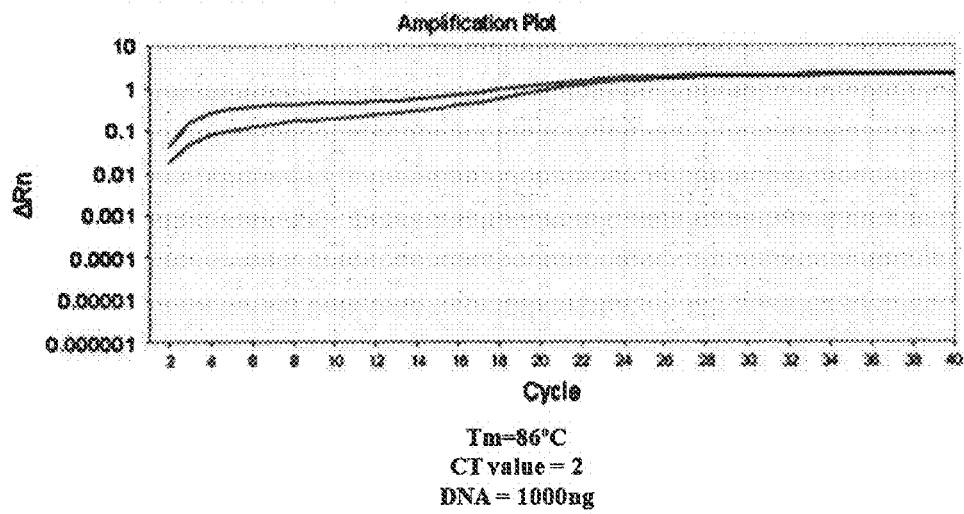
Tm=86°C
CT value = 2
DNA = 1000ng
Fig 7 (b): Melting curve of Aspergillus genus specific (probe KS 5' 6FAM and 3'BHQ)
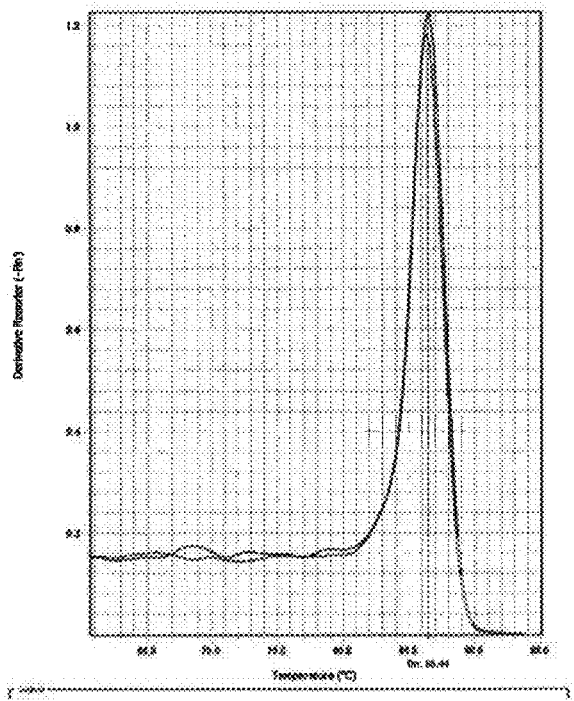

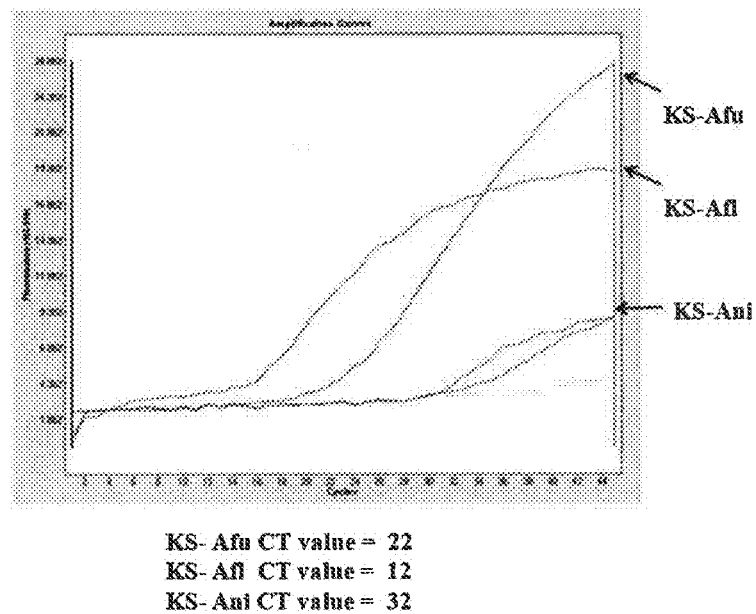
Fig 7 (c): Aspergillus genus specific (KS 5' 6FAM and 3'BHQ) Absolute amplification curve
KS- Afu CT value = 22
KS- Afl CT value = 12
KS- Ani CT value = 32

SEQUENCE LISTING

```
<160> NUMBER OF SEQ ID NOS: 18

<210> SEQ ID NO 1
<211> LENGTH: 29
<212> TYPE: DNA
<213> ORGANISM: Artificial
<220> FEATURE:
<223> OTHER INFORMATION: Primer, Y=CT

<400> SEQUENCE: 1
atctggagaa atgaytgcga tgcygcyat                              29

<210> SEQ ID NO 2
<211> LENGTH: 20
<212> TYPE: DNA
<213> ORGANISM: Artificial
<220> FEATURE:
<223> OTHER INFORMATION: Primer,  K=GT, Y=CT

<400> SEQUENCE: 2
tckagaccgg yatggttytc                                        20

<210> SEQ ID NO 3
<211> LENGTH: 26
<212> TYPE: DNA
<213> ORGANISM: Artificial
<220> FEATURE:
<223> OTHER INFORMATION: Probe, Y=CT, K=GT, B=CGT

<400> SEQUENCE: 3
```
aaccaygccg gtctkgaycg bggcca          26

<210> SEQ ID NO 4
<211> LENGTH: 26
<212> TYPE: DNA
<213> ORGANISM: Artificial
<220> FEATURE:
<223> OTHER INFORMATION: Primer

<400> SEQUENCE: 4
taagatgaag caaacatccg aggagt          26

<210> SEQ ID NO 5
<211> LENGTH: 21
<212> TYPE: DNA
<213> ORGANISM: Artificial
<220> FEATURE:
<223> OTHER INFORMATION: Primer

<400> SEQUENCE: 5
gcgggtggag agacctcagc t               21

<210> SEQ ID NO 6
<211> LENGTH: 25
<212> TYPE: DNA
<213> ORGANISM: Artificial
<220> FEATURE:
<223> OTHER INFORMATION: Probe

<400> SEQUENCE: 6
gtgcaacctc tgatcctacg ttggc           25

<210> SEQ ID NO 7
<211> LENGTH: 25
<212> TYPE: DNA
<213> ORGANISM: Artificial
<220> FEATURE:
<223> OTHER INFORMATION: Primer

<400> SEQUENCE: 7
cgattgatca caagttggct cgaac           25

<210> SEQ ID NO 8
<211> LENGTH: 31
<212> TYPE: DNA
<213> ORGANISM: Artificial
<220> FEATURE:
<223> OTHER INFORMATION: Primer

<400> SEQUENCE: 8
tacatgttgc cagattcctc atattccta g     31

<210> SEQ ID NO 9
<211> LENGTH: 25
<212> TYPE: DNA
<213> ORGANISM: Artificial
<220> FEATURE:
<223> OTHER INFORMATION: Probe

<400> SEQUENCE: 9
gcgccaaatg gtccagaagt atgtc           25

<210> SEQ ID NO 10
<211> LENGTH: 30
<212> TYPE: DNA
<213> ORGANISM: Artificial

<220> FEATURE:
<223> OTHER INFORMATION: Primer

<400> SEQUENCE: 10
caacgcaaaa tatggctact atctcgatca                30

<210> SEQ ID NO 11
<211> LENGTH: 26
<212> TYPE: DNA
<213> ORGANISM: Artificial
<220> FEATURE:
<223> OTHER INFORMATION: Primer

<400> SEQUENCE: 11
cattgatttc ttccagggtg attccg                    26

<210> SEQ ID NO 12
<211> LENGTH: 28
<212> TYPE: DNA
<213> ORGANISM: Artificial
<220> FEATURE:
<223> OTHER INFORMATION: Probe

<400> SEQUENCE: 12
gaagcttctt ccacatctca ggcaagga                  28

<210> SEQ ID NO 13
<211> LENGTH: 560
<212> TYPE: DNA
<213> ORGANISM: Aspergillus

<400> SEQUENCE: 13
gcttgaggtc tcctgtaagg aagcccatca taatttcttg attgaaagcg atttggtcca    60
gttgattaac cattgtgcct tgtctagacg gtaagatgaa gcaaacatcc gaggagtatg   120
ttcccgggga agctacagag gaggtaactg cagaagcaag tgcaacctct gatcctacgt   180
tggcgaatgc ggcctacact gaactccagg acggccctct tgacgccggt gctacagcag   240
ccaacgagat tgactcctct gcgcctaaag ctgaggtctc tccacccgcg cagactctcg   300
tttccgatgc tgctaatcct gtagccgagg cgtcgtggga acagaacggg gctggctcgc   360
tcgagtcgtc ggcaaatgct gacggctggg ttgaggtgcc tcgcgacccg gcggagacgg   420
agacgggcct acaggccacc cctgcctctg tcgataccgg tctgaaggac aaccagactg   480
tcgctgcggc ctccggacag agtgatgaac atgtctccgt gcctaaggcg cagggcagcg   540
acggattcga acccgttgtg                                              560

<210> SEQ ID NO 14
<211> LENGTH: 180
<212> TYPE: PRT
<213> ORGANISM: Aspergillus flavus

<400> SEQUENCE: 14

Thr Leu Leu Glu Gln Val Arg Leu Asp Leu Val Glu Thr Gly Leu Pro
1               5                   10                  15

Arg Leu Leu Gln Ser Arg Gln Val Lys Ser Val Thr Ile Val Pro Phe
            20                  25                  30

Leu Thr Arg Met Asn Glu Thr Met Ser Asn Ile Leu Pro Val Ser Phe
        35                  40                  45

Ile Ser Thr Glu Thr Arg Thr Asp Thr Gly Arg Ala Ile Pro Ala Ser
    50                  55                  60

```
Gly Arg Pro Gly Ala Gly Lys Cys Lys Leu Ala Ile Val Ser Met Ser
 65                  70                  75                  80

Gly Arg Phe Pro Glu Ser Pro Thr Thr Glu Ser Phe Trp Asp Leu Leu
                 85                  90                  95

Tyr Lys Gly Leu Asp Val Cys Lys Glu Val Pro Arg Arg Arg Trp Asp
                100                 105                 110

Ile Asn Thr His Val Asp Pro Ser Gly Lys Ala Arg Asn Lys Gly Ala
            115                 120                 125

Thr Lys Trp Gly Cys Trp Leu Asp Phe Ser Gly Phe Asp Pro Arg
130                 135                 140

Phe Phe Gly Ile Ser Pro Lys Glu Ala Pro Gln Met Asp Pro Ala Gln
145                 150                 155                 160

Arg Met Ala Leu Met Ser Thr Tyr Glu Ala Met Glu Arg Ala Gly Leu
                165                 170                 175

Val Pro Asp Thr
            180

<210> SEQ ID NO 15
<211> LENGTH: 177
<212> TYPE: PRT
<213> ORGANISM: Aspergillus niger

<400> SEQUENCE: 15

Pro Asp Lys Thr Tyr Leu Leu Ala Gly Gly Leu Gly Gly Leu Gly Arg
1               5                   10                  15

Thr Leu Ala Glu Trp Met Leu Gln Arg Asn Ala Lys His Leu Val Phe
                20                  25                  30

Leu Ser Arg Ser Gly Glu Thr Arg Ala Glu Lys Ala Thr Val Ser
            35                  40                  45

Trp Leu Arg Ala His Gly Ile Asp Val Thr Val Tyr Lys Gly Asp Val
 50                  55                  60

Ala Asn Pro Ala Asp Val Gln Ala Cys Val Gly Gly Ile Arg Asn Leu
 65                  70                  75                  80

Gly Gly Val Phe His Ala Ala Met Val Leu Asp Ala Ala Leu Glu
                 85                  90                  95

Asn Met Thr Tyr Ala Gln Trp His Gln Cys Val Gln Pro Lys Val Val
                100                 105                 110

Gly Ala Phe Asn Leu His Gln Ala Thr Lys Ser Leu Pro Leu Asp Phe
            115                 120                 125

Phe Val Thr Phe Ser Ser Val Ser Ala Cys Phe Gly Thr Arg Ser Gln
130                 135                 140

Gly Asn Tyr Ala Ala Ala Asn Thr Tyr Leu Asp Ala Leu Met Arg Tyr
145                 150                 155                 160

Arg Arg Gln Ile Gly Leu Pro Ala Ala Thr Met Asn Cys Gly Arg Ile
                165                 170                 175

Thr

<210> SEQ ID NO 16
<211> LENGTH: 270
<212> TYPE: PRT
<213> ORGANISM: Aspergillus fumigatus

<400> SEQUENCE: 16

Gln Asp Ile Asp Thr Tyr Phe Ile Pro Gly Gly Asn Arg Ala Phe Thr
1               5                   10                  15

Pro Gly Arg Ile Asn Tyr Tyr Phe Lys Phe Ser Gly Pro Ser Val Ser
```

```
                20                  25                  30
Val Asp Thr Ala Cys Ser Ser Ser Leu Ala Ala Ile His Leu Ala Cys
            35                  40                  45
Asn Ala Ile Trp Arg Asn Asp Cys Asp Thr Ala Ile Ser Gly Gly Val
 50                  55                  60
Asn Leu Leu Thr Asn Pro Asp Asn His Ala Gly Leu Asp Arg Gly His
 65                  70                  75                  80
Phe Leu Ser Arg Thr Gly Asn Cys Asn Thr Phe Asp Asp Gly Ala Asp
                85                  90                  95
Gly Tyr Cys Arg Ala Asp Gly Val Gly Thr Ile Val Leu Lys Arg Leu
            100                 105                 110
Glu Asp Ala Glu Ala Asp Asn Asp Pro Ile Leu Gly Val Ile Asn Ala
            115                 120                 125
Ala Tyr Thr Asn His Ser Ala Glu Ala Val Ser Ile Thr Arg Pro His
            130                 135                 140
Val Gly Ala Gln Ala Phe Ile Phe Asn Lys Leu Leu Asn Asp Thr Asn
145                 150                 155                 160
Thr Asn Pro His Glu Ile Gly Tyr Val Glu Met His Gly Thr Gly Thr
                165                 170                 175
Gln Ala Gly Asp Ala Val Glu Met Gln Ser Val Leu Asp Val Phe Ala
            180                 185                 190
Pro Asp Tyr Arg Arg Gly Pro Ala Asn Ser Leu Tyr Leu Gly Ser Ala
            195                 200                 205
Lys Ser Asn Ile Gly His Gly Glu Ser Ala Ser Gly Val Thr Ser Leu
            210                 215                 220
Val Lys Val Leu Leu Met Leu Lys Gln Asn Met Ile Pro Pro His Cys
225                 230                 235                 240
Gly Ile Lys Thr Lys Ile Asn His Asn Phe Pro Thr Asp Leu Ala Gln
                245                 250                 255
Arg Asn Val His Ile Ala Phe Lys Pro Thr Pro Trp Asn Arg
            260                 265                 270

<210> SEQ ID NO 17
<211> LENGTH: 280
<212> TYPE: PRT
<213> ORGANISM: Aspergillus flavus

<400> SEQUENCE: 17

Thr Ser Asp Asp Tyr Arg Glu Ile Asn Ser Gly Gln Asp Ile Asp Thr
 1                   5                  10                  15
Tyr Phe Ile Pro Gly Gly Asn Arg Ala Phe Thr Pro Gly Arg Ile Asn
                20                  25                  30
Tyr Tyr Phe Lys Phe Ser Gly Pro Ser Val Ser Val Asp Thr Ala Cys
            35                  40                  45
Ser Ser Ser Leu Ala Ala Ile His Met Ala Cys Asn Ser Ile Trp Arg
 50                  55                  60
Asn Asp Cys Asp Ala Ala Ile Ala Gly Gly Val Asn Ile Leu Thr Asn
 65                  70                  75                  80
Pro Asp Asn His Ala Gly Leu Asp Arg Gly His Phe Leu Ser Arg Thr
                85                  90                  95
Gly Asn Cys Asn Thr Phe Asp Asp Gly Ala Asp Gly Tyr Cys Arg Ala
            100                 105                 110
Asp Gly Val Gly Thr Ile Ile Leu Lys Arg Leu Glu Asp Ala Gln Ala
            115                 120                 125
```

```
Asp Asn Asp Pro Ile Leu Gly Val Ile Asn Gly Ala Tyr Thr Asn His
130                 135                 140

Ser Ala Glu Ala Val Ser Ile Thr Arg Pro His Val Gly Ala Gln Ala
145                 150                 155                 160

Phe Ile Phe Asn Lys Leu Leu Asn Asp Ala Asn Ile Asp Pro Lys Asp
                165                 170                 175

Val Ser Tyr Val Glu Met His Gly Thr Gly Thr Gln Ala Gly Asp Ala
                180                 185                 190

Val Glu Met Gln Ser Val Leu Asp Thr Phe Ala Pro Asp Tyr Arg Arg
                195                 200                 205

Gly Pro Gly Gln Ser Leu His Leu Gly Ser Ala Lys Ala Asn Val Gly
210                 215                 220

His Gly Glu Ser Ala Ser Gly Val Thr Ala Leu Val Lys Val Leu Leu
225                 230                 235                 240

Met Met Lys Lys Asn Thr Ile Pro Pro His Cys Gly Ile Lys Thr Lys
                245                 250                 255

Ile Asn His Asn Phe Pro Thr Asp Leu Ala Gln Arg Asn Val His Ile
                260                 265                 270

Ala Phe Gln Pro Thr Pro Trp Asn
                275                 280

<210> SEQ ID NO 18
<211> LENGTH: 300
<212> TYPE: PRT
<213> ORGANISM: Aspergillus niger

<400> SEQUENCE: 18

Asn Arg Ala Phe Thr Pro Gly Arg Ile Asn Tyr Tyr Phe Lys Phe Ser
1               5                   10                  15

Gly Pro Ser Val Ser Val Asp Thr Ala Cys Ser Ser Ser Leu Ala Ala
                20                  25                  30

Ile His Met Ala Cys Asn Ser Ile Trp Arg Asn Asp Cys Asp Ala Ala
                35                  40                  45

Ile Thr Gly Gly Val Asn Ile Leu Thr Ser Pro Asp Asn His Ala Gly
50                  55                  60

Leu Asp Arg Gly His Phe Leu Ser Thr Thr Gly Asn Cys Asn Thr Phe
65                  70                  75                  80

Asp Asp Gly Ala Asp Gly Tyr Cys Arg Ala Asp Gly Val Gly Ser Ile
                85                  90                  95

Val Leu Lys Arg Leu Glu Asp Ala Glu Ala Asp Asn Asp Pro Ile Leu
                100                 105                 110

Ala Val Ile Asn Gly Ala Tyr Thr Asn His Ser Ala Glu Ala Val Ser
                115                 120                 125

Ile Thr Arg Pro His Val Gly Ala Gln Ala Phe Ile Phe Asn Lys Leu
                130                 135                 140

Leu Asn Asp Ala Asn Ile Asp Pro Lys Asp Val Ser Tyr Val Glu Met
145                 150                 155                 160

His Gly Thr Gly Thr Gln Ala Gly Asp Ala Val Glu Met Gln Ser Val
                165                 170                 175

Leu Asp Val Phe Ala Pro Asp Tyr Arg Arg Gly Pro Gly Gln Ser Leu
                180                 185                 190

His Ile Gly Ser Ala Lys Ala Asn Ile Gly His Gly Glu Ser Ala Ser
                195                 200                 205

Gly Val Thr Ala Leu Val Lys Val Leu Leu Met Met Arg Glu Asn Met
210                 215                 220
```

-continued

```
Ile Pro Pro His Cys Gly Ile Lys Thr Lys Ile Asn Ser Asn Phe Pro
225                 230                 235                 240

Thr Asp Leu Ala Lys Arg Asn Val His Ile Ala Phe Gln Pro Thr Pro
            245                 250                 255

Trp Asn Arg Pro Ala Ser Gly Lys Arg Arg Thr Phe Val Asn Asn Phe
            260                 265                 270

Ser Ala Ala Gly Gly Asn Thr Ala Leu Leu Leu Glu Asp Ala Pro Ile
        275                 280                 285

Pro Glu Arg Gln Gly Gln Asp Pro Arg Ser Phe His
    290                 295                 300
```

DIAGNOSTIC ASSAYS FOR THE DETECTION AND IDENTIFICATION OF ASPERGILLI

FIELD OF INVENTION

The present invention relates to PCR based simultaneous detection of *A. fumigatus, A. flavus* and *A. niger* in clinical and agricultural samples. The diagnostic assays use specific primers and fluorescent based quantitative PCR assays and facilitate (i) detection of Melanin producing *A. fumigatus*, Aflatoxin producing *A. flavus* from *A. niger* from Agricultural samples and (ii) for specific detection and differentiation of *Aspergillus fumigatus, Aspergillus flavus* and *Aspergillus niger* in the clinical samples.

BACKGROUND

*Aspergillus* species, *A. fumigatus, A. flavus* and *A. niger* are the causative agents in human "Aspergillosis" and are also pathogens damaging Agricultural crops. They induce a variety of *Aspergillus* induced clinical conditions in immunocompetent and immunocompromised hosts. Depending on the host's immunity and the virulence of the clinical spectrum varies from aspergilloma, allergic *Aspergillus* sinusitis, allergic bronchopulmonary aspergillosis [ABPA], and hypersensitivity pneumonitis and invasive aspergillosis (Agarwal R. Allergic bronchopulmonary aspergillosis. Chest. 2009 March;135(3):805-26). These infections are often and progress fast and eventually fatal in immunocompromised patients. For example, pulmonary and cerebral aspergillosis has mortality rates of 86 and 99% respectively, even when adequately treated (Marr K A, Bowden R A. Fungal infections in patients undergoing blood and marrow transplantation. Transpl Infect Dis. 1999 December; 1(4):237-46). Allergic bronchopulmonary Aspergillosis in immunocompetent persons is often diagnosed by serological tests based on *Aspegillus* antigens and the specific IgE and IgG antibodies in the serum samples. Serodiagnostic tests based on Antigenic peptides and antigens are reported (Denning D W. Therapeutic outcome in invasive aspergillosis. Clin Infect Dis. 1996 September;23(3):608-15). In case of invasive Aspergillosis, particularly in immunocompromised host, the antibodies are present either negligible quantities or absent. Hence detection of circulating antigen or pathogen in clinical samples is the best strategy. This necessitates the development of dependable, specific methods for the detection of pathogens in clinical samples. In view of this efforts are made to develop more sensitive reagents and protocols for detection of important *Aspergillus* species in clinical samples.

Gene based methods are reported in the literature for detection of *A. fumigatus, A. flavus* and *A. niger* for clinical samples. They are mainly based on ITS regions of *Aspergillus* species which are genus specific (Abdin M Z, Ahmad M M, Javed S. Advances in molecular detection of *Aspergillus:* an update. Arch Microbiol. 2010 June;192(6):409-25. Epub 2010 Apr. 1). Further some of the important *Aspergillus* species such as *Aspergillus fumigatus* has been reported to develop resistance to Amphotericin and itraconazole. The need for a rapid test to identify *Aspergilli* to the species level, to assist in the selection of appropriate drugs for the treatment of clinical *Aspergillus* infections is also of high importance. Nonculture-based methods are increasingly used for rapid, accurate diagnosis to improve the Outcome of patient. New and existing DNA amplification platforms have high sensitivity and specificity for direct detection and identification of fungi in clinical specimens. Novel technologies (e.g., isothermal and PNA FISH methods), platforms enabling high-throughput analyses (e.g., DNA microarrays and Luminex xMAP) and/or commercial PCR assays are some of advances in diagnosis of Aspergillosis (Spiess B, Seifarth W, Hummel M, Frank O, Fabarius A, Zheng C, Mörz H, Hehlmann R, Buchheidt D. DNA microarray-based detection and identification of fungal pathogens in clinical samples from neutropenic patients. J Clin Microbiol. 2007 November;45(11): 3743-53. Epub 2007 Aug. 22).

Unique internal transcribed sequence 2 (ITS2) coding regions have been used to develop nucleic acid probes for different species of *Aspergillus* (*A. flavus, A. fumigatus, A. niger, A. terreus,* and *A. nidulans*), as disclosed in U.S. Pat. No. 6,372,430 (U.S. Pat. No. 6,372,430—Nucleic acids for detecting *Aspergillus* species and other filamentous fungi). Real time PCR methodologies using ITS region in *Aspergilli* has also been described for specific detection from clinical samples and Agri products (Schabereiter-Gurtner C, Selitsch B, Rotter M L, Hirschl A M, Willinger B Development of novel real-time PCR assays for detection and differentiation of eleven medically important *Aspergillus* and *Candida* species in clinical specimens. J Clin Microbiol. 2007 March;45 (3):906-14, Ramirez M, Castro C, Palomares J C, Torres M J, Aller A I, Ruiz M, Aznar J, Martín-Mazuelos E. Molecular detection and identification of *Aspergillus* spp. from clinical samples using real-time PCR.Mycoses. 2009 March;52(2): 129-34, Faber J, Moritz N, Henninger N, Zepp F, Knuf M. Rapid detection of common pathogenic *Aspergillus* species by a novel real-time PCR approach.Mycoses. 2009 May;52 (3):228-33, Bolehovska R, Pliskova L, Buchta V, Cerman J, Hamal P. Detection of *Aspergillus* spp. in biological samples by real-time PCR. Biomed Pap Med Fac Univ Palacky Olomouc Czech Repub. 2006 November;150(2):245-8, Mulè G, Susca A, Logrieco A, Stea G, Visconti A.Development of a quantitative real-time PCR assay for the detection of *Aspergillus carbonarius* in grapes. Int J Food Microbiol. 2006 Sep. 1;111 Suppl 1:S28-34). Recently a high throughput assay based on Luminex xMAP hybridization technology has been described for clinically relevant fungal pathogens including *Aspergillus* species (Etienne K A, Kano R, Balajee S A. Development and validation of a microsphere-based Luminex assay for rapid identification of clinically relevant aspergilli. J Clin Microbiol. 2009 April;47(4):1096-100). Monochrome LightCycler real-time PCR based on fluorescence probe have also been described for specific quantification of *Aspergillus* (Bu R, Sathiapalan R K, Ibrahim M M, Al-Mohsen I, Almodavar E, Gutierrez M I, Bhatia K. Monochrome LightCycler PCR assay for detection and quantification of five common species of *Candida* and *Aspergillus*. J Med Microbiol. 2005 March;54(Pt 3):243-248, Imhof A, Schaer C, Schoedon G, Schaer D J, Walter R B, Schaffner A, Schneemann M. Rapid detection of pathogenic fungi from clinical specimens using LightCycler real-time fluorescence PCR.Eur J Clin Microbiol Infect Dis. 2003 Sep;22(9):558-60). Some of the methods such as DNA microarrays are also reported for detection of *Aspergillus* species from clinical samples (Spiess B, Seifarth W, Hummel M, Frank O, Fabarius A, Zheng C, Mörz H, Hehlmann R, Buchheidt D. DNA microarray-based detection and identification of fungal pathogens in clinical samples from neutropenic patients. J Clin Microbiol. 2007 November;45(11):3743-53) but these are expensive to perform and require sophisticated analytical tools to interpret the results. However all these tests are based on internal transcribed sequence and spacer regions between 28S rRNA and 18srRNA sequences. Genes of important enzymes in the mycotoxin biosynthetic pathway can be good targets for diagnostic tests as it will not only assure the presence of fungus but can also tell us about the mycotoxin production for the same gene which will add to specificity and sensitivity of the test (Baird R, Abbas H K, Windham G, Williams P, Baird S, Ma P, Kelley R, Hawkins L, Scruggs M. Identification of Select Fumonisin Forming *Fusarium* Species Using PCR Applications of the Polyketide Synthase Gene and its Relationship to Fumonisin Production in vitro. Int J Mol Sci. 2008 April;9(4):554-70, Atoui A, Mathieu F, Lebrihi A. Targeting a polyketide synthase gene for *Aspergillus carbonarius* quantification and ochratoxin A assessment in grapes using real-time PCR. Int J Food Microbiol. 2007 Apr. 20;115(3):313-8).

In the current invention a diagnostic assay for detection and identification of important *Aspergillus* species based on the gene of a key enzyme in polyketide biochemical pathway is developed, which will also add to specificity and sensitivity of the test. Potential mycotoxin production can be detected by PCR which may permit the establishment of critical control points and is a significant advantage. *Aspergillus* species are known to produce a wide range of secondary metabolites, under certain environmental conditions. Some of the important polyketides produced by *Aspergillus* species include Melanin pigments from *A. fumigatus* and carcinogenic mycotoxins Aflatoxins from *A. flavus*. Melanin is considered a virulent factor of *Aspergillus fumigatus*. *Aspergillus flavus* is also known to be an opportunistic pathogen of agricultural crops such as maize, cotton, groundnuts, rice, chillies and contaminate them with Aflatoxins and Sterigmatocystin. FAO approved permeable limits of Aflatoxin in agri products are 4-20 ppb in different countries (Jelinek C F, Pohland A E, Wood G E. Worldwide occurrence of mycotoxins in foods and feeds—an update. J Assoc Off Anal Chem. 1989 March-April;72(2):223-30). *A. niger* is also reported to produce ochratoxins, which contaminates nuts and coffee beans. Ochratoxin A, a polyketide product is teratogenic in rat, hamster and chick embryo and is an inhibitor of hepatic mitochondrial transport systems. It has also been reported to cause damage to the liver, gut, lymphoid tissue and renal tubular damage (Chulze S N, Magnoli C E, Dalcero A M. Occurrence of ochratoxin A in wine and ochratoxigenic mycoflora in grapes and dried vine fruits in South America.Int J Food Microbiol. 2006 Sep. 1; 111 Suppl 1:S5-9).

Diversity in end product produced by polyketide biosynthetic pathway by each *Aspergillus* species suggests the possible diversity in the structure and function of important enzymes such as Polyketide Synthase. Polykide synthase is key enzyme in the biochemical pathway responsible for production of polyketides and they are highly diverse in *Aspergillus* species. Polyketide Synthases of *Aspergillus* species are multidomain and multifuncational proteins of approximately 3000 amino acids with 7 to 9 domains encoded by a single gene (Schümann J, Hertweck C. Advances in cloning, functional analysis and heterologous expression of fungal polyketide synthase genes. J Biotechnol. 2006 Aug. 5; 124(4):690-703, Bhetariya P., Madan T, Varma A., Basir S, Sarma P U. Allergens/Antigens, Toxins and Polyketides of Important *Aspergillus* Species. Indian Journal of Clinical Biochemistry, June 2011. Vol. 26(2)104-119). The domains of the enzyme facilitate different steps in the synthesis of various intermediates of polyketide products. There are few domains essential for the minimal functional role of PKS while other domains are responsible for post polyketide modifications. Bioinformatics analysis of these Polyketide synthase domain sequences revealed conserved motifs and some non conserved sequences in the PKS domains. Based on the sequence analysis of these Polyketide synthases, sequences were identified and change in the sequences was identified. Information has been used to develop the diagnostic test for *Aspergillus fumigatus*, *Aspergillus flavus* and *Aspergillus niger* in Agriculture samples for detection and identification of *Aspergillus* infections. Nucleotide sequences are selected and modified and probes have been developed for detection of *Aspergillus* species relevance to human and agriculture.

OBJECTIVES OF THE INVENTION

The objective of the present invention is to provide a PCR based simultaneous detection of *Aspergillus* species.

SUMMARY

Accordingly, the present invention provides a PCR based detection of *Aspergillus* species involving a conserved region of domain sequences from Polyketide synthase gene useful for detection and identification of important *Aspergillus* species. The diagnostic assay is based on identification of conserved region of domain sequences from Polyketide synthase gene useful for detection and identification of important *Aspergillus* species.

BRIEF DESCRIPTION OF FIGURES AND TABLES

Table 1: Sequence ID of primers and probes used in the study.

Table 2: *Aspergillus* Strains and isolates used in the study.

FIG. 1 (*a*): KS F-R primers gradient PCR with *A. fumigatus*,

FIG. 1 (*b*): KS F-R primers gradient PCR with *A. flavus*,

FIG. 1 (*c*): KS F-R primers gradient PCR with *A. niger*,

FIG. 2 (*a*): Specific amplification of *A. fumigatus*, *A. flavus* and *A. niger* using specific primers.

FIG. 2 (*b*): Gradient PCR for specific primers with (a) *A. flavus* (b) *A. fumigatus* and (c) *A. niger*.

FIG. 3. Multiplex PCR for *A. fumigatus*, *A. flavus* and *A. niger*.

FIG. 4 (*a*): *Aspergillus fumigatus* specific SYBR green Real time PCR.

FIG. 4 (*b*): Melting curve of *Aspergillus fumigatus* specific SYBR green Real time PCR.

FIG. 4 (*c*): *Aspergillus fumigatus* specific (probe Afu 5' 6-FAM & 3'BHQ) Absolute amplification curve.

FIG. 5 (*a*): *Aspergillus flavus* specific SYBR green real time PCR.

FIG. 5 (*b*): Melting curve of *Aspergillus flavus* specific SYBR green real time PCR.

FIG. 5 (*c*): *Aspergillus flavus* specific (probe Afl 5' HEX and 3'BHQ) Absolute amplification curve.

FIG. 6 (*a*): *Aspergillus niger* specific SYBR green Real time PCR.

FIG. 6 (*b*): Melting curve of *Aspergillus niger* specific SYBR green real time PCR.

FIG. 6 (*c*): *Aspergillus niger* specific (probe 5' Ani TET and 3' BHQ) Absolute amplification curve.

FIG. 7 (*a*): *Aspergillus* genus specific SYBR green Real time PCR.

FIG. 7 (*b*): Melting curve of *Aspergillus* genus specific (probe KS 5' 6FAM and 3'BHQ).

FIG. 7 (*c*): *Aspergillus* genus specific (KS 5' 6FAM and 3'BHQ) Absolute amplification curve.

DETAILED DESCRIPTION OF THE INVENTION

In the present work, PKS gene sequences of three important *Aspergillus* species *A. fumigatus*, *A. flauvs* and *A. niger* are aligned and analyzed. It was found that different species of *Aspergillus* have similar sequences or conserved region in the domains of PKS gene as well as some non-conserved region in domains of PKS gene. Sequence of PKS gene is represented by SEQ ID NO. 13. Specific primers and probes are developed based on the analysis for detection of *A. fumigatus, A. flavus* and *A. niger* together and specifically. *Aspergillus fumigatus* is a major contributing agent in systemic fungal infections and is often encountered in patients with organ transplants, acute leukemia. *A. flavus* and *A. niger* are also frequently reported in invasive cases in the recent past. *Aspergillus flavus* is an agricultural pathogen contributing to contaminations of carcinogenic Aflatoxins in groundnut, maize, cotton and tree nuts. A positive correlation between aflatoxin contamination of agricultural commodities and primary human hepatocellular carcinoma has been well documented (Food Addit Contam Part A Chem Anal Control Expo Risk Assess. 2009 February; 26(2):180-8). *A. niger* produced teratogenic mycotoxin ochratoxin A in coffee, nuts etc. A few immunologic tests exist for detection of these *Aspergillus* species with limited sensitivity and specificity. Polymerase chain reaction tests based on useful gene sequences in a ribosomal intergenic spacer region for *Aspergillus* species are reported which is genus specific and lacks species specificity (Rath P M, Ansorg R. Identification of medically important *Aspergillus* species by single strand conformational polymorphism (SSCP) of the PCR-amplified intergenic spacer region. Mycoses; 2000; 43(11-12):381-6). In recent efforts metabolic pathways are being examined for presence of fungi particularly on the mycotoxin producing potential of *Aspergillus* species. Probes are being designed based on mycotoxin biosynthetic pathway such as multiplex PCR is reported for Aflatoxin producers *Aspergillus flavus*, and *Aspergillus parasaticus* based on nor-1, ver-1, omt-A genes of aflatoxin (and sterigmatocystin) biosynthesis (Klingspor L, Loeffler J. *Aspergillus* PCR formidable challenges and progress. Med Mycol. 2009;47 Suppl 1:S241-7, Degola F, Berni E, Dall'Asta C, Spotti E, Marchelli R, Ferrero I, Restivo F M. A multiplex RT-PCR approach to detect aflatoxigenic strains of *Aspergillus flavus*. J Appl Microbiol. 2007 August;103(2):409-17.). It is well documented that there is a quantitative correlation between toxin production and biomass in naturally contaminated materials (Criseo G, Bagnara A, Bisignano G. Differentiation of aflatoxin-producing and non-producing strains of *Aspergillus flavus* group. Lett Appl Microbiol. 2001 October;33(4):291-5). Quantitative PCR systems do not use end point measurement to quantify the amount of target molecules present in the samples, while real time PCR systems detect the precise amount of target molecule present in the sample. This technology will be useful for determining associations between detection of a gene at critical control points in food production and quantification of the mycotoxin in the final product.

TaqMan™ technology uses 5'-3' exonuclease activity of polymerase to generate a template specific fluorescent signal after hydrolyzing an internal probe during each step of the PCR. The internal probe is 5' labeled with a reporter fluorescent dye and 3' ligated to a quencher dye; they are located in close proximity on the internal probe. The quencher dye greatly reduces the fluorescent emitted by the reporter dye by FRET. During PCR, the reporter dye is separated from the quencher Dye which results in an increase of the reporter dye signal. Only if the internal probe is binding to the DNA in between the two PCR primers a fluorescence signal during PCR is generated. Here an additional hybridization step increases the specificity of the PCR. Combining the quantitative detection and advantage of TaqMan™ technology a sensitive and specific test can be developed which will indicate the presence of target molecule such as fungi itself and their potential to produce mycotoxin in the samples.

In the present invention the sequences identified from PKS domains are modified and fluorescent probes are prepared to use for identification of *Aspergillus fumigatus, Aspergillus flavus* and *Aspergillus niger*. Probe for detection of three *Aspergilli* together such as *Aspergillus fumigatus, Aspergillus flavus* and *Aspergillus nigeri* based on conserved region in PKS domain is developed. Probe for *Aspergillus fumigatus* is specifically based on unique gene identified earlier (TMS33), Probe for detection of *Aspergillus flavus* is based on Polyketide synthase A protein (XP_002379951.1) and probe for detection of *Aspergillus niger* is based on Polyketide synthase protein (XP_001393884.2).

In an embodiment of the present invention oligonucleotide useful for the detection of *Aspergillus* species selected from the group consisting of SEQ ID NO.1-12.

In an embodiment of the present invention wherein SEQ ID NO. 1,2,4,5,7,8,10,11 are primers useful for PCR based detection of *Aspergillus* species.

In an embodiment of the present invention wherein SEQ ID NO. 3,6,9,12 are probes for PCR based detection of *Aspergillus* species.

In an embodiment of the present invention wherein the *Aspergillus* species is selected from the group comprising of *A. fumigatus, A. flavus* and *A. niger*.

In another embodiment of the present invention provides a PCR based method for the detection of *Aspergillus* species comprising the steps of:
 a. isolating genomic DNA from the sample by known methods,
 b. designing primers having SEQ ID NO. 1, 2.
 c. performing Real time PCR using primers obtained in step b,
 d. optionally performing multiplex PCR using primers and probes having SEQ ID NO. 1,2,4,5,7,8,10,11.
 e. detecting and measuring the amount of amplified DNA.

In another embodiment of the present invention wherein the *Aspergillus* species is selected from the group comprising of *A. fumigatus, A. flavus* and *A. niger*.

In another embodiment of the present invention the sequence detected is the polyketide synthase domain.

In another embodiment of the present invention the probe for detecting the nucleic acid sequence set forth as SEQ ID NO: 4,5,6 (forward primer, reverse primer and Taqman probe) from *A. fumigatus* specifically based on unique gene of *A. fumigatus*.

In another embodiment of the present invention the probe for detecting the nucleic acid sequence set forth as SEQ ID NO: 7,8,9 (forward primer, reverse primer and Taqman probe) from *A. flavus* specifically.

In another embodiment of the present invention the probe for detecting the nucleic acid sequence set forth as SEQ ID NO: 10, 11, 12 (forward primer, reverse primer and Taqman probe) from *A. niger* specifically.

In another embodiment of the present invention wherein detecting the domain of Polyketide synthase gene nucleic acid sequence comprises use of a nucleic acid probe from the *Aspergilli* such as *Aspergillus fumigatus, Aspergillus flavus* and *Aspergillus niger*.

In yet another embodiment of the present invention a kit for the diagnosis of *Aspergillus* species said kit comprising primers of SEQ ID NO. 1, 2, 4, 5, 7, 8, 10, 11 and probes of SEQ ID NO. 3, 6, 9, 12 optionally along with instructions manual.

In yet another embodiment of the present invention a kit for the diagnosis of *Aspergillus* species said kit comprising of:

I. A primer set comprising a forward primer having SEQ ID NO. 1 and a reverse primer having SEQ ID NO. 2 wherein said forward primer and said reverse primer is capable of generating a PCR amplicon from a region of Polyketide synthase gene, II. A probe having SEQ ID NO. 3 capable of hybridizing to said PCR amplicon.

Based on genome sequences of *Aspergillus fumigatus, Aspergillus flavus* and *Aspergillus niger* from NCBI, Polyketide synthase protein sequences are retrieved and aligned. The domains for PKS are searched by CDD search at NCBI and also by SEARCH PKs software available online. The sequences are then aligned by clustal X software. The conserved motifs in each domain are derived. One particular domain is selected which is highly conserved in these three fungi, the conserved motifs are derived by careful analysis of multiple alignment results. Up to 150 specific Amino acid sequences are taken and it is converted into nucleotide sequences by available universal amino acid code. Two degenerate primers are designed from these regions; degeneracy is taken care of by manually aligning the primer sequences. Primers are checked by BLAST. PCR conditions are optimized and primers are tested for specific amplification of product from *A. fumigatus, A. flavus* and *A. niger*. PCR is also tested for negative control such as *Fusarium* species. Around 60 samples are checked by this PCR from different isolates of *A. fumigatus, A. flavus* and *A. niger*. TaqMan™ probe sequence is developed and checked for specific amplification.

From *A. fumigatus* a unique EST (TMS33, Gene ID: DN626065.1) is identified and reported (Upadhyay S, Shankar J, Madan T, Basir S, Sarma P U. Expressed sequence tags of *Aspergillus fumigatus*: extension of catalogue and their evaluation as putative drug targets and/or diagnostic markers. Indian Journal of Clinical Biochemistry, 2009/24 (2) 131-136). Gene sequence [Gene ID: 3507735 (AFUA_1G07280)] is taken from NCBI. It is hypothetical protein which does not have homology with any other fungi. Primers are designed and PCR conditions are optimized. DNA amplifications are performed using *A. fumgiatus* DNA. A product of 180 bp is amplified from *A. fumigatus* isolates.

Aflatoxin is a known carcinogenic mycotoxin for humans as well as animals. Aflatxins are synthesized by condensation of acetate units; their synthesis is estimated to involve at least 16 different enzymes. The enzymes and their gene sequences for aflatoxin biosynthetic pathway are now known. Polyketide SynthaseA (PKSA) is important in conservation of Acetate to Polyketide molecule, Norsolonic acid, one of stable intermediate of Aflatoxin Biosynthetic pathway. PKSA sequence from *A. flavus* and *A. parasiticus* are 98% homologous. PKSA protein (XP_002379951.1) from *A. flavus* is aligned with other PKS proteins of *A. flavus, A. fumigatus* and *A. niger* using with clustal X software. Non homologous region from PKSA is derived by careful analysis of the sequences. Selected amino acid sequences are translated into nucleotide sequences. Primers are designed and PCR conditions are optimized for amplification for specific product from *A. flavus*. PCR is also checked for non-specific amplification from *A. fumigatus* and *A. niger*. Amplification has been checked in toxigenic as well atoxigenic strains of *Aspergillus flavus*. TaqMan™ probe sequence is developed and checked for specific amplification. *A. flavus* isolates from ITCC (Indian type culture collection) are collected, amplified and DNA is isolated.

PKSN (XP_001394705.1) from *A. niger* is aligned other PKS proteins of *A. flavus, A. fumigatus* and *A. niger* using with clustal X software. Non homologous region from PKSN is derived by careful analysis of the sequences. Selected amino acid sequences are translated into nucleotide sequences. Primers are designed and PCR conditions are optimized for specific amplification of DNA of *A. niger*. PCR is also checked for non-specific amplification from *A. fumigatus* and *A. flavus*. TaqMan™ probe sequence is developed and checked for specific amplification of *Aspergillus* species.

The basic method for detection of *A. fumigatus, A. flavus* and *A. niger* is summarized as follows:

1. Providing a template for the amplification of polyketide synthase gene from *Aspergillus fumigatus, Aspergillus flavus* and *Aspergillus niger* for the detection. DNA is isolated from the clinical as well as agricultural samples as described in the protocol.
2. Adding primers as shown in table 1 (SEQ ID NO. 1,2,4, 5,7,8,10,11) for conducting multiplex PCR using the template obtained in step 1 for the amplification of polyketide synthase gene.
3. Conditions used are 5 min initial step, followed by 35 cycles at 94° C. for 1 min, 56.7° C. for 1 min and 72° C. for 1.5 min and a final extension step at 72° C. for 5 min.
4. Obtaining a detection of amplified product from *A. fumigatus, A. flavus* and *A. niger* by known method.

Optionally method of detection of the *A. fumigatus, A. flavus* and *A. niger* is as follow.

5. Providing a template for the amplification of polyketide synthase gene from

*Aspergillus fumigatus, Aspergillus flavus* and *Aspergillus niger* for the detection. DNA template is isolated from the clinical as well as agricultural samples as described in the protocol.

6. Adding primers and probes as shown in table 1 (SEQ ID NO. 1,2,3, 4,5,6,7,8,9,10,11,12) for conducting multiplex real time PCR using the template obtained in step 1.
7. Conditions used are 50 cycles at 95° C. for 15 s and 60° C. for 1 min each, in ABI Real time PCR model 77005.
8. Obtaining a detection of amplified product from *A. fumigatus, A. flavus* and *A. niger* by known method.

Details of sequences of polyketide synthase gene and proteins from various *Aspergillus* species are as follows:

Gene Sequences

```
GCTTGAGGTCTCCTGTAAGGAAGCCCATCATAATTTCTTGATTGAAAGCG
ATTTGGTCCAGTTGATTAACCATTGTGCCTTGTCTAGACGGTAAGATGAA
GCAAACATCCGAGGAGTATGTTCCCGGGGAAGCTACAGAGGAGGTAACTG
CAGAAGCAAGTGCAACCTCTGATCCTACGTTGGCGAATGCGGCCTACACT
GAACTCCAGGACGGCCCTCTTGACGCCGGTGCTACAGCAGCCAACGAGAT
TGACTCCTCTGCGCCTAAAGCTGAGGTCTCTCCACCCGCGCAGACTCTCG
TTTCCGATGCTGCTAATCCTGTAGCCGAGGCGTCGTGGGAACAGAACGGG
GCTGGCTCGCTCGAGTCGTCGGCAAATGCTGACGGCTGGGTTGAGGTGCC
TCGCGACCCGGCGGAGACGGAGACGGGCCTACAGGCCACCCCTGCCTCTG
TCGATACCGGTCTGAAGGACAACCAGACTGTCGCTGCGGCCTCCGGACAG
AGTGATGAACATGTCTCCGTGCCTAAGGCGCAGGGCAGCGACGGATTCGA
ACCCGTTGTG
```

Protein Sequences

```
SEQ ID No. 14:
ref|XP_002379951.1| aflC/pksA/pksL1/polyketide synthase [Aspergillus
flavus NRRL3357] (311-394)
>tlleqvrldl vetglprllq srqvksvtiv pfltrmnetm snilpvsfis tetrtdtgra ipasgrpgag kcklaivsms grfpesptte sfwdllykgl dvckevprrr wdinthvdps gkarnkgatk wgcwldfsge fdprffgisp keapqmdpaq rmalmstyea meraglvpdt SEQ ID No. 15:
ref|XP_001398521.2| polyketide synthase [Aspergillus niger CBS 513.88]
(1956-2132)
>pdktyllagglgglgrtlaewmlqrnakhlvflsrsgetraeakatvswlrahgidvtvykgdvanpadvqacvggirnlggvfha amvladaalenmtyaqwhqcvqpkvvgafnlhqatkslpldffvtfssvsacfgtrsqgnyaaantyldalmryrrqiglpaatmn cgrit SEQ ID No. 16:
gi|71002828|ref|XP_756095.1| conidial pigment polyketide synthase
PksP/Alb1 [Aspergillus fumigatus Af293]
> qdidtyfipg gnraftpgri nyyfkfsgpsvsvdtacsss laaihlacna iwrndcdtai sggvnlltnp dnhagldrgh flsrtgncntfddgadgycr adgvgtivlk rledaeadnd pilgvinaay tnhsaeavsi trphvgaqafifnkllndtn tnpheigyve mhgtgtqagd avemqsvldv fapdyrrgpa nslylgsaksnighgesasg vtslvkvllm lkqnmipphc giktkinhnf ptdlaqrnvh iafkptpwnr SEQ ID No. 17:
gi|238503167|ref|XP_002382817.1| polyketide synthetase PksP [Aspergillus
flavus NRRL3357]
>tsddyreins gqdidtyfip ggnraftpgr inyyfkfsgpsvsvdtacss slaaihmacn siwrndcdaa iaggvniltn pdnhagldrg hflsrtgncntfddgadgyc radgvgtiil krledaqadn dpilgvinga ytnhsaeays itrphvgaqa fifnkllnda nidpkdvsyv emhgtgtqag davemqsvld tfapdyrrgp gqslhlgsakanvghgesas gvtalvkvll mmkkntipph cgiktkinhn fptdlaqrnv hiafqptpwn SEQ ID No. 18:
gi|317031606|ref|XP_001393884.2| conidial yellow pigment biosynthesis
polyketide synthase [Aspergillus niger CBS 513.88]
>nraftpgrin yyfkfsgpsv svdtacsssl aaihmacnsiwrndcdaait ggvniltspd nhagldrghf lsttgncntf ddgadgycra dgvgsivlkrledaeadndp ilavingayt nhsaeavsit rphvgaqafi fnkllndani dpkdvsyvemhgtgtqagda vemqsvldvf apdyrrgpgq slhigsakan ighgesasgv talvkvllmm renmipphcg iktkinsnfp tdlakrnvhi afqptpwnrp asgkrrtfvn nfsaaggnta llledapipe rqgqdprsfh
```

EXAMPLES

The following examples are given by way of illustration of the present invention and therefore should not be construed to limit the scope of the present invention Examples 1

Isolation of Fungal DNA

*Aspergillus* isolates are grown on SDA Broth (Sabouraud Dextrose Broth) (Himedia) for 3-5 days at 37° C. degree to generate fungal growth for DNA extraction.

Fungal biomass/mycelia are harvested after 3 days, filtered and washed several times with sterile distilled water. Mycelial mat is transferred into a pre-cooled (−20.degree C.) sterile ceramic mortar, flushed with liquid nitrogen, and slowly ground with a pestle into a fine powder. Four grams wet weight of mycelia paste is collected in a 15 ml polypropylene screw cap tube (Falcons, Germany). Fungal cells are suspended in 4 ml of 10mM phosphate buffer, pH 6.0 and incubated with 0.5 U chitinase per gram wet weight of cells at 25° C. for 90 mins At the end of the incubation period, equal volume of lysis buffer (50 mM Tris-cl, 50 mM EDTA, 3% SDS, 1% β-mercaptoethanol pH 7.2) is added and the suspension is incubated at 65° C. in a water bath for 1 hour. Subsequently, the contents of the polypropylene tube are subjected to heat treatment in a microwave oven for 3 sec each for three times.

The cell lysate is extracted with phenol:chloroform:isoamylalcohol (25:24:1) and the DNA in the aqueous layer is precipitated with two volumens of ethyl alcohol in the presence of 0.1M sodium acetate. DNA is washed with 70% ethanol, dried and dissolved in TE buffer (10 mM Tris-Cl, 1 mM EDTA, pH 8). The DNA sample is then treated with RNase A (50 μg/ml) for 30 min at 37° C. The sample is extracted with phenol:chloform:isoamylalcohol and precipitated with ethanol as above. The DNA is dissolved in TE buffer and the concentration is determined spectrophotometrically. Quality of the DNA is also checked by gel electrophoresis. The powder is suspended in Lysis Buffer (Containing Tris, EDTA, RNAse) containing RNase (Sigma Chemical Co., St. Louis, Mo.), and transferred into an Oak Ridge centrifugation tube (Nalge Nunc International, Rochester, N.Y.). A rapid method for extraction of genomic DNA based on the cleavage of chitin with chitinase is developed in house (Bir N, Paliwal A, Muralidhar K, Reddy P, Sarma P U. A rapid method for the isolation of genomic DNA from *Aspergillus fumigatus*. Prep Biochem. 1995 November; 25(4):171-81).

Extraction of *Aspergillus* DNA from Biological Samples

The sputa and bronchial aspirates are incubated with 1% pancreatin at room temperature for 1 hour. The fluidized samples are centrifuged at 3500×g for 20 mins. Pellets are washes with 1 ml of 0.1 M phosphate buffer and recentrifuged. Swabs are taken from the pellets and investigated for the presence of *Aspergillus fumigatus* by culture. The pellet is suspended in 0.2 ml of 0.1 M phosphate buffer, pH 6.8. Control specimens from healthy individuals are also processed under similar conditions.

Aliquots from suspended pellets are taken in eppendrof tubes and 0.5 U of chitinase is added to each tube and incubated for 1 hour at 25° C. tubes are then heated in a microwave oven for 3 s cycles each. Debris from the chitinase treated sputa and bronchial aspirate is pelleted by centrifugation at 12,000×g for 10 min The supernatant is siphoned off and the pellet is emulsified by vigorous vortexing in 100 µl if chloroform. Distilled water (50 µl) is added and emulsified with the chloroform phase. After centrifugation at 12,000×g for 10 min, the upper aqueous phase is collected. The samples containing the chromosomal DNA are stored at −20° C. with choloroform, and are recentrifuged prior to use.

Extraction of DNA from Agricultural Samples.

Two grams of agricultural produce (e.g. ground nut seeds) is resuspended in 10 ml of SDA broth and incubated in 50-ml sterile Falcon tubes on an orbital shaker with gentle agitation (50 rpm) at 37° C. for 48 hours. After incubation, the tube contents are centrifuged (5 min at 5,000 3 g) and the pellets are frozen in liquid nitrogen. From suspension blends, 2-ml portions are taken and total DNA is extracted by the above-described procedure.

Preparation of Primers and Probes

All primers and probes are synthesized by automated DNA synthesizer (Lab India, ABI Prism).

TABLE 1

Sequence ID of primers and probes used in the study.

| Sequence ID no. | Sequence ID/name | Primer/probe sequence | Species | Amplification product |
|---|---|---|---|---|
| 1 | KS-F | ATCTGGAGAAATGAYTGCGATGCYGCY AT* | *A. fumigatus, A. flavus and A. niger* | 200 bp |
| 2 | KS-R | TCKAGACCGGYATGGTTYTC* | *A. fumigatus, A. flavus and A. niger* | |
| 3 | KS-probe | 6-FAM 5'AACCAYGCCGGTCTKGAYCGBGGCC A3' BHQ1* | *A. fumigatus, A. flavus and A. niger* | |
| 4 | Afu F | TAAGATGAAGCAAACATCCGAGGAGT | *A. fumigatus* | 180 bp |
| 5 | Afu R | GCGGGTGGAGAGACCTCAGCT | *A. fumigatus* | |
| 6 | AfuProbe | 6-FAM5'GTGCAACCTCTGATCCTACGTTG GC3'BHQ1 | *A. fumigatus* | |
| 7 | AflF | CGATTGATCACAAGTTGGCTCGAAC | *A. flavus* | 250 bp |
| 8 | AflR | TACATGTTGCCAGATTCCTCATATTCCC TAG | " | |
| 9 | Aflprobe | HEX-5' GCGCCAAATGGTCCAGAAGTATGTC 3'BHQ1 | " | |
| 10 | AniF | CAACGCAAAA'TATGGCTACT'ATCTCG ATCA | *A. niger* | 110 bp |
| 11 | AniR | CATTGATTTCTTCCAGGGTGATTCCG | " | |
| 12 | AniProbe | TET-5' GAAGCTTCTTCCACATCTCAGGCAAGG A3'BHQ1 | " | |

*R = AG, Y = CT, M = AC, K = GT, W = AT, S = CG, B = CGT, D = AGT, H = ACT, V = ACG, N = ACGT

1) A conserved region of Polyketide synthase domain is identified by multiple alignments of Polyketide synthases gene from *A. fumigatus* (XP_756095.1), *A. flavus* (XP_002382817.1) and *A. niger* (XP_001398521.2). Primers are designed and PCR conditions are optimized (table 1). DNA amplifications are performed A product of 200 bp is amplified from *A. fumigatus, A. flavus* and *A. niger* (FIG. 1*a*, 1*b* and 1*c*), and table 2). The Taqman™ probe specific for *A. fumigatus, A. flavus* and *A. niger* is designed (SEQ ID NO. 1,2,3) by following the general rules outlined by the manufacturer using Primer Express software, version 2.0 and are synthesized at Biochem ltd. A probe detecting *A. fumigatus, A. flavus* and *A. niger* specific 200 bp amplicon contained the reporter dye FAM covalently attached to the 5' end and the quencher BHQ at 3' Taqman™ assay is carried out in 50-µl volume reactions, with the additions 12.5 µl of TaqMan Universal Master Mix, 2.5 µl of forward and reverse primers (10 nM each), 2.5 µl of TaqMan probe, 2.5 µl of 2 mg/ml bovine serum albumin, fraction V and 5 µl of DNA template. Standard procedures for the operation of the model 7700 as described in the PerkinElmer instrument's manual, are followed. The temperature cycling (50 cycles at 95° C. for 15 s and 60° C. for 1 min each) is performed in a 96-well thermal cycler. Each amplification run contained several negative controls. Amplification data collected by the 7700 Sequence Detector are then analyzed by the use of the Sequence Detection System software. The fractional cycle number reflecting a positive PCR result is called the cycle threshold (Ct). Control sample without DNA template is included in the experiment runs as negative control. All samples except the controls are tested in duplicate; the control is tested in triplicate (FIG. 7*a*, 7*b* and 7*c*, table 2).

2) A unique EST (TMS33, Gene ID: DN626065.1) from *A. fumigatus* is identified and reported (28). Gene sequence (Gene ID: 3507735 (AFUA_1G07280) is taken from NCBI. Primers are designed and PCR conditions are optimized. DNA amplifications are performed. A product of 180 bp is amplified from *A. fumigatus* (FIG. 2*a*, 2*b*). The Taqman™ probe specific for *A. fumigatus* is designed (SEQ ID NO. 4,5,6) by following the general rules outlined by the manufacturer using Primer Express software, version 2.0 and are synthesized at Biochem Ltd. A probe detecting *A. fumigatus* specific 180 bp amplicon contained the reporter dye FAM covalently attached to the 5' end and the quencher BHQ attached to the 3'. The Taqman™ assay is carried out in 50-µl volume reactions with the additions 12.5 µl A of TaqMan Universal Master Mix, 2.5 µl of forward and reverse primers (10 nM each), 2.5 µl of TaqMan probe, 2.5 µl of 2 mg/ml bovine serum albumin, fraction V and 5 µl of DNA template. Standard procedures for the operation of the model 7700 as described in the perkin almer instrument's manual, are followed. The temperature cycling (50 cycles at 95° C. for 15 s and 59° C. for 1 min each) is performed in a 96-well thermal cycler. Each amplification run contained several negative controls. Amplification data collected by the 7700 Sequence Detector are then analyzed by the use of the Sequence Detection System software. The fractional cycle number reflecting a positive PCR result is called the cycle threshold (Ct). Control sample without DNA template is included in the experiment runs as negative control. All samples except the controls are tested in duplicate; the control is tested in triplicate (FIG. 4*a*, 4*b*, 4*c*, table 2).

3) A region of Polyketide synthase A protein sequence from *A. flavus* (accession no.:—XP_002379951.1) is taken from NCBI. Selected AA sequences are converted to nucleotide sequences by DNASTAR software. Primers are designed and PCR conditions are optimized. DNA amplifications are performed. A product of 250 bp is amplified from *A. flavus* (FIG. 2*a*, 2*b*). The Taqman™ probe specific for A. flavus is designed (SEQ ID NO. 7,8,9) by following the general rules outlined by the manufacturer using Primer Express software, version 2.0 and are synthesized at Lab India. A probe detecting *A. flavus* specific 250 bp amplicon contained the reporter dye HEX covalently attached to the 5' end and the quencher BHQ at 3'. The Taqman™ assay is carried out in 50-µl volume reactions with the additions 12.5

TABLE 2

*Aspergillus* Strains and isolates used in the study

| S. No. | Strains | ATCC NO. | Source | Multiplex PCR | Real time PCR results |
|---|---|---|---|---|---|
| | | Strains used for Primers and probe design | | | |
| 1 | *Aspergillus fumigatus* | *Aspergillus fumigatus* Af293 | Patient lung suffering from IA | − | − |
| 2 | *Aspergillus flavus* | *Aspergillus flavus* NRRL3357 | Cotton seed | − | − |
| 3 | *Aspergillus niger* | *Aspergillus niger* CBS 513.88 | — | − | − |
| | | Strains used for PCR and Real time PCR | | | |
| 1. | *Aspergillus flavus* | NRRL18079 | Cotton seeds | + | + |
| 2. | *Aspergillus flavus* | NRRL2211 | — | + | + |
| 3. | *Aspergillus flavus* | MTCC 1884 | Vegetable waste | − | + |
| 4. | *Aspergillus fumigatus* | ATCC13073 | | + | + |
| 5. | *Aspergillius fumigatus* | ITCC2550 (MTCC no) | Uranium waste | + | + |
| 6. | *Aspergillius fumigatus* | MTCC No. 7132 | Mangroove soil | + | + |
| 7. | *Aspergillus niger* | ITCC2218.95 | Apple orchard | − | + |
| 8. | *Aspergillus niger* | ATCC9029 | — | + | + |
| 9. | *Aspergillius niger* | ATCC6275 | — | + | + |

µl of TaqMan Universal Master Mix, 2.5 µl of forward and reverse primers (10 nM each), 2.5 µl of TaqMan probe, 2.5 µl of 2 mg/ml bovine serum albumin, fraction V and 5 µl of DNA template. Standard procedures for the operation of the model 7700 as described in the perkin almer instrument's manual, are followed. The temperature cycling (50 cycles at 95° C. for 15 s and 59° C. for 1 min each) is performed in a 96-well thermal cycler. Each amplification run contained several negative controls. Amplification data collected by the 7700 Sequence Detector are then analyzed by the use of the Sequence Detection System software. The fractional cycle number reflecting a positive PCR result is called the cycle threshold (Ct). Control sample without DNA template is included in the experiment runs as negative control. All samples except the controls are tested in duplicate; the control is tested in triplicate (FIG. 5a, 5b, table 2).

4) A region of Polyketide synthase protein sequence from *A. niger* (accession no.:—XP_001398521.2) is taken from NCBI. Selected AA sequences are converted to nucleotides.

Primers are designed and PCR conditions are optimized. DNA amplifications are performed. A product of 110 bp is amplified from *A. niger* (FIG. 2a, 2b). The Taqman™ probe specific for *A. niger* is designed (SEQ ID NO. 10,11,12) by following the general rules outlined by the manufacturer using Primer Express software, version 2.0 and are synthesized at Lab India. A probe detecting *A. niger* specific 110 bp amplicon contained the reporter dye TET covalently attached to the 5' end and the quencher BHQ attached to the 3'. The Taqman™ assay is carried out in 50-µl volume reactions with the additions 12.5 µl of TaqMan Universal Master Mix, 2.5 µl of forward and reverse primers (10 nM each), 2.5 µl of TaqMan probe, 2.5 µl of 2 mg/ml bovine serum albumin, fraction V and 5 µl of DNA template. Standard procedures for the operation of the model 7700 as described in the perkin almer instrument's manual, are followed. The temperature cycling (50 cycles at 95° C. for 15 s and 59° C. for 1 min each) is performed in a 96-well thermal cycler. Each amplification run contained several negative controls. Amplification data collected by the 7700 Sequence Detector are then analyzed by the use of the Sequence Detection System software. The fractional cycle number reflecting a positive PCR result is called the cycle threshold (Ct). Control sample without DNA template is included in the experiment runs as negative control. All samples except the controls are tested in duplicate; the control is tested in triplicate (FIG. 6a, 6b).

Quantification of Real Time PCR

The fractional cycle number reflecting a positive PCR result is called the cycle threshold (Ct). Control sample without DNA template is included in the experiment runs as negative control. Absolute Quantification of *Aspergillus fumigatus, Aspergillus flavus* and *Aspergillus niger* by $C_T$ method as determined from TaqMan analysis.

Quantification is performed by first subtracting mean reference sequence $C_T$ values from target sequence $C_T$ values for both test samples and a pre specified calibrator sample to obtain Delta $C_T$ values.

ADVANTAGES OF THE INVENTION

1. The PCR based simultaneous detection of *A. fumigatus, A. flavus* and *A. niger* from any biological samples is very useful diagnostic method.
2. The method can indicate the toxigenic potential of the organism based on the gene amplification.
3. The method is economical compared to other available immunoassays.
4. The method is faster and can be applicable for screening of large number of samples.

We claim:

1. A kit for the detection of *Aspergillus* species, said kit comprising as primers the oligonucleotides of SEQ ID NO. 1, 2, 4, 5, 7, 8, 10 and 11, and as probes the oligonucleotides SEQ ID NOS: 3, 6, 9 and 12, wherein each probe contains a fluorescent label, with instructions for use of said oligonucleotides for detection of *Aspergillus* species.

2. A set of oligonucleotides useful for the detection of *Aspergillus* species containing oligonucleotides SEQ ID NOS: 1, 2, 4, 5, 7, 8, 10 and 11 as primers for PCR-based detection of *Aspergillus* species and oligonucleotides SEQ ID NOS: 3, 6, 9, and 12 as probes for PCR-based detection of *Aspergillus* species, wherein each probe contains a fluorescent label.

3. A PCR-based method for the detection of *Aspergillus* species comprising the steps of:
   a. providing DNA from a sample and
   b. performing multiplex PCR on said DNA using as primers the oligonucleotides SEQ ID NOS: 1, 2, 4, 5, 7, 8, 10 and 11, and
   c. detecting the PCR amplification products.

4. The method of claim 3 wherein the PCR amplification products are detected using as probes the oligonucleotides SEQ ID NOS: 3, 6, 9 and 12, wherein each probe contains a fluorescent label.

* * * * *